(12) United States Patent
Latterell (10) Patent No.: US 10,363,082 B2
(45) Date of Patent: Jul. 30, 2019

(54) ELECTROSURGICAL DEVICE

(75) Inventor: Scott T. Latterell, Hermosa Beach, CA (US)

(73) Assignee: TTUMED LLC, Minneapolis, MN (US)

( * ) Notice: Subject to any disclaimer, the term of this patent is extended or adjusted under 35 U.S.C. 154(b) by 1761 days.

(21) Appl. No.: 12/444,190

(22) PCT Filed: Oct. 5, 2007

(86) PCT No.: PCT/US2007/080593
§ 371 (c)(1),
(2), (4) Date: Apr. 13, 2010

(87) PCT Pub. No.: WO2008/043074
PCT Pub. Date: Apr. 10, 2008

(65) Prior Publication Data
US 2010/0211065 A1    Aug. 19, 2010

Related U.S. Application Data

(60) Provisional application No. 60/849,369, filed on Oct. 5, 2006.

(51) Int. Cl.
*A61B 18/04* (2006.01)
*A61B 18/14* (2006.01)
(Continued)

(52) U.S. Cl.
CPC ........ *A61B 18/042* (2013.01); *A61B 18/1492* (2013.01); *A61B 18/16* (2013.01);
(Continued)

(58) Field of Classification Search
CPC ...... A61B 18/1492; A61B 2018/00214; A61B 2018/1465; A61B 18/16;
(Continued)

(56) References Cited

U.S. PATENT DOCUMENTS 5,617,854 A * 4/1997 Munsif ............. A61B 18/1492
600/374
5,681,282 A 10/1997 Eggers et al.
(Continued)

FOREIGN PATENT DOCUMENTS

EP    1095627 A1    5/2001
GB    2313062    11/1997
(Continued)

OTHER PUBLICATIONS

Extended European Search Report from EP Application No. 07843922. 1, corresponding to U.S. Appl. No. 12/444,190, dated Sep. 15, 2011 pp. 1-8.
(Continued)

*Primary Examiner* — Linda C Dvorak
*Assistant Examiner* — Samantha M Good
(74) *Attorney, Agent, or Firm* — Pauly, DeVries Smith & Deffner LLC (57) ABSTRACT

An electrosurgical assembly is disclosed, the assembly having two, three or more electrodes configured to provide advantageous tissue removal and precision for conducting electrosurgical procedures, including improved ablation and coagulation of tissue. The electrodes are configured and arranged so that energy can be applied in a highly uniform and precise fashion, depending upon the application. In addition, the electrosurgical assembly allows flexibility in use by, in some embodiments, allowing selective switching of the active and return electrodes, and also selective switching between ablation and coagulation modes. In certain embodiments the invention includes one or more electrodes having the ability to undergo changes in shape.

23 Claims, 6 Drawing Sheets

(51) Int. Cl.
*A61B 18/00* (2006.01)
*A61B 18/16* (2006.01)

(52) U.S. Cl.
CPC ............... *A61B 2018/00214* (2013.01); *A61B 2018/00267* (2013.01); *A61B 2018/00916* (2013.01); *A61B 2018/1465* (2013.01); *A61B 2018/1467* (2013.01)

(58) Field of Classification Search
CPC ........... A61B 2018/00267; A61B 2018/00547; A61B 2018/00916; A61B 2018/1467; A61B 18/042
USPC .................. 606/32, 34, 37, 39–42, 45–50
See application file for complete search history.

(56) References Cited

U.S. PATENT DOCUMENTS

| | | | |
|---|---|---|---|
| 5,697,281 A | 12/1997 | Eggers et al. | |
| 5,697,536 A | 12/1997 | Eggers et al. | |
| 5,843,019 A | 12/1998 | Eggers et al. | |
| 5,944,715 A | 8/1999 | Goble et al. | |
| 6,004,319 A | 12/1999 | Goble et al. | |
| 6,011,995 A | 1/2000 | Guglielmi et al. | |
| 6,013,076 A | 1/2000 | Goble et al. | |
| 6,014,589 A | 1/2000 | Farley et al. | |
| 6,056,744 A | 5/2000 | Edwards | |
| 6,063,079 A * | 5/2000 | Hovda ............... | A61B 18/1402 128/898 |
| 6,090,108 A | 7/2000 | McBrayer et al. | |
| 6,113,597 A | 9/2000 | Eggers et al. | |
| 6,149,620 A | 11/2000 | Baker et al. | |
| 6,228,078 B1 | 5/2001 | Eggers et al. | |
| 6,287,304 B1 | 9/2001 | Eggers et al. | |
| 6,544,258 B2 | 4/2003 | Fleenor et al. | |
| 6,837,884 B2 * | 1/2005 | Woloszko ....................... | 606/32 |
| 6,939,309 B1 | 9/2005 | Beatty et al. | |
| 6,966,907 B2 | 11/2005 | Goble | |
| 2001/0029366 A1 * | 10/2001 | Swanson et al. ............... | 606/29 |
| 2002/0173784 A1 * | 11/2002 | Sliwa et al. .................... | 606/28 |
| 2003/0014051 A1 | 1/2003 | Woloszko | |
| 2003/0032953 A1 | 2/2003 | Vandusseldorp et al. | |
| 2003/0130572 A1 * | 7/2003 | Phan et al. ..................... | 600/374 |
| 2003/0225403 A1 * | 12/2003 | Woloszko ............ | A61B 18/148 606/41 |
| 2005/0080409 A1 | 4/2005 | Young et al. | |
| 2005/0107781 A1 * | 5/2005 | Ostrovsky et al. ............. | 606/41 |
| 2005/0119647 A1 * | 6/2005 | He et al. ......................... | 606/41 |
| 2005/0251134 A1 | 11/2005 | Woloszko et al. | |
| 2006/0189971 A1 | 8/2006 | Tasto et al. | |
| 2007/0173809 A1 | 7/2007 | Goble | |

FOREIGN PATENT DOCUMENTS

| | | |
|---|---|---|
| WO | 00/62698 | 10/2000 |
| WO | 2004/086994 | 10/2004 |

OTHER PUBLICATIONS

PCT Search Report and Written Opinion (Corrected), from corresponding International Application No. PCT/US07/80593, dated Jun. 25, 2008 (11 pages).

Japanese Office Action, from corresponding Japanese Application No. 2009-531626, dated Aug. 8, 2012, English translation, pp. 1-8.

* cited by examiner

ELECTROSURGICAL DEVICE

This application is being filed as a PCT International Patent application on Oct. 5, 2007, applicant and inventor, Scott T. Latterell, a U.S. Citizen, is an applicant for the purposes of the United States only, and claims priority to U.S. Patent Application Ser. No. 60/849,369, titled "Shapeable Vaporization Catheter", filed Oct. 5, 2006; the contents of which are herein incorporated by reference.

TECHNICAL FIELD

The present technology relates to medical devices. Particularly, the present technology relates to electrosurgical devices.

BACKGROUND

Electrosurgery is the application of electrical current to tissue for the purpose of surgically altering the tissue. It is a method commonly used for a variety of medical procedures including, but not limited to, resecting or vaporizing tissue (typically by ablation) associated with warts, benign tumors, and tissue growth such as that associated with Benign Prostatic Hyperplasia (BPH). During such procedures, electrosurgery can also be used for controlling bleeding through coagulation. Electrosurgical devices generally operate by providing electrical current traveling from an active electrode through target tissue to a return electrode. Depending on the characteristics of the energy (voltage, frequency, wattage, for example) being passed through the tissue, and the device electrodes (size, shape, distance, for example), the tissue can be transected, vaporized or coagulated.

Traditionally there have been two primary types of electrosurgical equipment: bipolar and monopolar. Bipolar electrosurgery provides the active and return electrode on the surgical device itself in close proximity to the targeted site, while monopolar electrosurgery provides only the active electrode at the targeted site, and the return electrode is generally a conductive plate that is secured to the patient's outer skin surface. In monopolar electrosurgery higher voltages are required to overcome the associated resistance of the patient's body, which serves as a necessary part of the circuit. In bipolar electrosurgery, less input power is needed, but the effect on the targeted tissue is limited by a number of factors, including the proximity of the active to the return electrode, the size and shape of the electrodes, the shape and regularity of the electric field that is created, and the ratio of the surface area of the return electrode to the surface area of the active electrode.

Although present electrosurgery equipment and techniques are suitable for many applications, a need remains for equipment and techniques that offer improved ablation and coagulation and greater control over the ablation and coagulation processes.

SUMMARY

The technology disclosed herein provides for an electrosurgical apparatus that offers improved control and precision in removal of tissue.

In some embodiments the invention includes an electrosurgical apparatus having one active electrode and two return electrodes, the return electrodes are typically positioned on opposite ends of the active electrode so as to provide balanced current flow (as appropriate, or controlled imbalanced current flow as desired) and improved performance with regard to tissue removal, as well as coagulation of tissue as desired.

The present invention, by providing (in certain embodiments) a central active electrode intermediate two return electrodes, offers significant improvements over preexisting electrosurgical devices. One problem with prior electrosurgical devices is that they often have relatively small active electrodes, a problem that can be countered using the designs of the present invention. Size and shape of prior electrodes has been restricted due to issues with near field and far field distances, as well as issues associated with current density. For example, when the active and return electrodes are too close to one another, then near field issues become prominent and the electrodes can arc and be destroyed. When the electrodes are too far apart, or have a surface area that is too large, then far field issues arise causing problems with initiation and creation of a uniform plasma zone around the active electrode. Far field issues also often require higher power levels.

Existing devices, such as many bipolar electrosurgical devices, often suffer from slow tissue removal rates (less than 1 g/min). This is due, in part, to the return surface area to active surface area ratio requiring that the active electrode be substantially smaller than the return electrode to provide the current density required if reliable initiation and maintaining of the plasma zone is to occur. Unfortunately, a small active surface area results in increased procedure time (costly and harder on patient); and reduced tissue removal. Simply increasing the active surface area does not solve this problem, because it inhibits initiation, reducing precision, and increasing the chance of patient injury due to unintended tissue damage. Also, increased active surface area requires more power to maintain high current density and counter increased far field distance.

Furthermore, coagulation/hemostasis is inconsistent and unreliable with existing devices because of inefficient flow of current. This problem is due to electrode design, and can arise during both vaporization (also known as ablation) and spot coagulation. This can result in additional blood loss; poor visibility and associated decreases in safety; potential for "re-bleeds" after the operation requiring additional intervention; and increased procedure time Electrode configurations of the present invention provide reduce far field distances and allow larger plasma zones resulting in a method of energy delivery that improves tissue removal rates, up to for example 50 percent, over existing devices, and provides consistent initiation and vaporization without more power required. The active zones can, in some embodiments, also be changed in shape and size, further improving performance in many implementations. These improvements also lead, in certain embodiments, to better hemostasis during vaporization due to the current flow which is deeper and broader; improved spot coagulation of bleeders because the hemostasis energy is delivered faster and broader, resulting in more consistent and reliable effect; and an opportunity for blended vaporization and coagulation energy delivery to further enhance performance.

The result, using the various embodiments of the present invention, allows for potentially reduced procedure time; greater tissue removal; improved visibility and safety; reduced blood loss; faster patient recovery and reduced patient complications.

The technology of the present invention offers medical practitioners improved views of the area in which tissue is being removed, and customizable active areas that allow a single electrosurgical apparatus to have multiple operational modes, including two or more tissue removal configurations and two or more coagulation configurations. The technology allows for changes in the shape of the electrosurgical apparatus, specifically changes in shape and orientation of the electrode surfaces, as well as changes in current delivered to the electrode assembly, so as to allow adjustments in performance and function.

In addition, in certain embodiments, the electrosurgical apparatus allows high tissue removal rates while still maintaining control and precision of the tissue removal. As noted earlier, in some embodiments the electrosurgical apparatus can be adjusted, during a surgical procedure, to modify the size and shape of the electrodes, as well as to adjust whether specific electrodes function as active or return electrodes. This allows, for example, a single electrosurgical apparatus to be switched between tissue removal at a tip surface of the apparatus or a side surface of the apparatus. For example, in some implementations the present invention uses three (or more) electrodes in a row. The active electrode is switched repeatedly between the distal (tip) electrode and a middle electrode. The other two (or more) electrodes are left as return electrodes, maintaining a high ratio of return surface area to active surface area. In the alternative, the active electrode can cycle through the three (or more) electrodes to generate an active surface at a larger area than would otherwise be possible from having a single fixed active electrode.

In some implementations one or more of the electrodes is expandable and/or flexible for good maneuverability and effectiveness when performing electrosurgery. For example, the apparatus may be inserted into small cavities and expanded when it reaches a localized operation site. This expandability may manifest itself in regard to having one or more electrodes that have a normal state that is modified before or after a surgical procedure begins. For example, in one implementation an electrode assembly having a first diameter is inserted into a patient and subsequently the diameter of the assembly is expanded. However, in other implementations the electrode assembly is contracted before insertion into a patient, and thereafter the assembly is allowed to expand within the patient.

The apparatus, through some embodiments, may be expanded in asymmetrical shapes to accommodate asymmetrical surgery locales, as well as to provide asymmetric tissue removal and coagulation.

According to example embodiments, the apparatus produces an electric field that is substantially symmetric and consistent from a substantially balanced and symmetric electrode placement. Additionally, in various embodiments, the ratio of the return electrode surface area to the active electrode surface area may be maximized by disposing a return electrode at least partially within an active electrode, using more than one return electrode in proximity of the active electrode, or both. Such configurations allow for fast, safe, and efficient electrosurgical procedures. It is also possible to apply coagulation and ablation frequencies simultaneously in those embodiments having multiple electrodes.

More specifically, the technology disclosed herein has, in certain embodiments, a first electrode that may contain a second electrode. The first electrode can partially surround the second electrode. The assembly may have an additional electrode on the proximal end of the first electrode and an additional electrode on the distal end of the first electrode, meaning that the electrode assembly includes (in some embodiments) a first electrode with additional electrodes on either ends of the first electrode.

Furthermore, the first electrode may have a shape and/or size that can be altered via a manipulation means that is in mechanical communication with the electrode, such that the diameter or other aspect of the first electrode can be altered. The disclosed configurations allow for an increase in the ratio of the return electrode surface area to the active electrode surface area relative to the prior art, a consistent and predictable electric field, an alterability of the proximity between the return and active electrodes, and/or an alterability of the shape of at least one electrode.

In one embodiment, the first electrode is a conductive woven material that has a circular cross-section that defines a central cavity. In another embodiment, the first electrode (typically the active electrode) is constructed of a woven conductive material and is substantially spherical in shape. In yet another embodiment, the first electrode comprises a conductive material in the shape of a helix.

As noted above, the apparatus itself may be attached to an electrosurgical generator unit through leads or wires, as is known in the art. The first electrode is optionally constructed so as to be flexible, and to define at least a partial cavity within the electrode, and has a proximal end and a distal end. The first electrode is not limited to a circular cross section, and may have a cross section of virtually any shape. The first electrode may be constructed of coiled wire, braided electrically conductive material, welded lattice, laser cut or machined lattice, woven electrically conductive material, any combination thereof, or other suitable electrically conductive material, especially when such material is able to be configured to be repeatedly expanded and contracted. However, it will be appreciated that the first electrode may be constructed out of coiled wire, braided material, woven material, etc. even when the first electrode is not configured to be expanded and contracted. The first electrode could also be constructed of any other material where structural flexibility is allowed for shape manipulation. The first electrode may have a lattice configuration, for example. Additionally, a cavity defined by the first electrode is not limited to a circular cross section, and also may have a cross section of virtually any shape.

Generally, the apparatus has at least a second electrode in addition to the first electrode, the second electrode at least partially disposed proximate to the first electrode, meaning that the second electrode may be disposed near the proximal end of the first electrode or near the distal end of the first electrode. The second electrode and the first electrode should not make direct conductive contact when the device is in operation, i.e. when a current is passing between them to remove or coagulate tissue, otherwise the apparatus will develop an electrical short. Generally a resistive material will be positioned between the electrodes to insulate them from each other. Additionally, at least a portion of the second electrode may be contained within the first electrode. There also can be a third electrode that is disposed proximate to the first electrode, meaning that the third electrode may be at least disposed on the proximal end of the first electrode or on the distal end of the first electrode. The third electrode and the first electrode may not generally make electrical contact. Additionally, at least a portion of the third electrode may be contained within the first electrode.

In some implementations of the invention, a manipulation means is in mechanical communication with the first electrode. The manipulation means may be a means of changing the diameter of the first electrode, or other electrodes. The manipulation means also may be a means of changing the shape of the first electrode, or other electrodes. The manipulation means may be a rod, screw, solenoid, or similar device that, when engaged, changes the shape (such as the diameter) of the first electrode by applying a force either directly or indirectly to the first electrode. The manipulation means may be engaged through a foot pedal, lever, button, valve, dial, nut, or any other applicable user-apparatus interface.

The above summary of the present invention is not intended to describe each discussed embodiment of the present invention. This is the purpose of the figures and the detailed description that follows.

BRIEF DESCRIPTION OF THE DRAWINGS

The technology will now be described in greater detail, by way of example, with references to the drawings, in which.

DETAILED DESCRIPTION

The technology disclosed herein provides for an electrosurgical apparatus that offers improved control and precision in removal of tissue. In some embodiments the electrosurgical apparatus can be adjusted, during a surgical procedure, to modify the size and shape of one or more of the electrodes. In addition, in certain embodiments, specific electrodes functioning as active or return electrodes can be changed during a surgical procedure, such as to change an active electrode into a passive electrode, or to change the frequency of electrical energy. In addition, in certain embodiments, the electrosurgical apparatus allows higher tissue removal rates while still maintaining control and precision.

In some implementations one or more of the electrodes is expandable for good maneuverability and effectiveness when performing electrosurgery. For example, the apparatus may be inserted into small cavities and expanded when it reaches a localized operation site. The apparatus, through some embodiments, may be expanded in asymmetrical shapes to accommodate asymmetrical surgery locales, as well as to provide asymmetric tissue removal. In the alternative, such expansion can be symmetric or substantially symmetric around a central axis.

Figure 1:
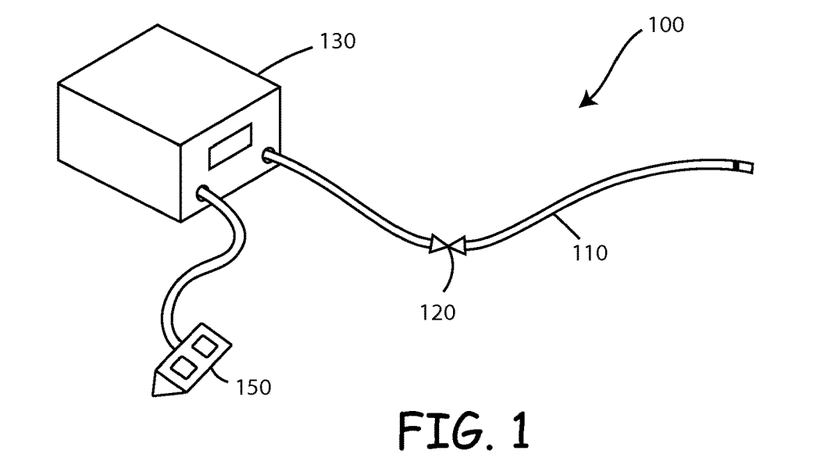
FIG. 1 is a perspective view of an overall system incorporating one embodiment of the apparatus disclosed herein.

Referring now to the figures, various embodiments of the invention will be described in greater detail. FIG. 1 is a perspective view of an example system incorporating one embodiment of an electrosurgical apparatus made in accordance with the invention. In this example embodiment, an electrosurgical apparatus 100 is connected to an electrosurgical generator 130. The connection can be made, for example, via a lead, cord, wire, or cable 110. A user-apparatus interface 120 may be disposed between the electrosurgical apparatus 100 and the electrosurgical generator 130. In the depicted embodiment, a foot pedal 150 is also connected to the electrosurgical generator 130 via a lead, cord, wire, or cable, for example, which may control output of the electrosurgical generator.

Figure 2A:
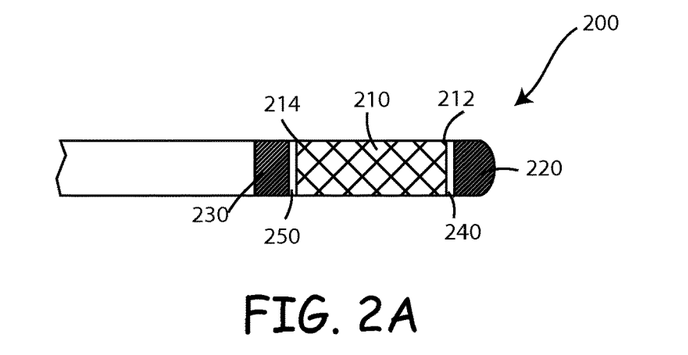
FIG. 2A is a side view of one embodiment of an electrode assembly constructed and arranged consistent with the technology claimed herein.

FIG. 2A shows a side view of one embodiment electrode assembly 200 constructed in accordance with the invention and consistent with the technology claimed herein. The assembly includes a first electrode 210. Near the first electrode 210 is a second electrode 220 disposed on the distal end 212 of the first electrode 210, at the tip of the electrode assembly 200. A first insulator 240 separates the first electrode 210 and the second electrode 220. Near the first electrode 210 is also a third electrode 230 positioned on the other end (the proximal end 214, which is opposite the tip of the assembly 200) of the first electrode 210. A second insulator 250 separates the first electrode 210 from the third electrode 230.

The first electrode 210 is constructed so as to be flexible, to define at least a partial cavity within the electrode, and has a distal end 212 and a proximal end 214. The first electrode 210 is not limited to a circular cross section, and may have a cross section of virtually any shape, including a shape that does not completely surround the assembly 200. The first electrode 210 may be at least partially constructed of coiled wire, braided electrically conductive material, woven electrically conductive material, or any combination thereof.

The first electrode 210 can also be at least partially constructed of any other conductive material where structural flexibility is allowed for shape manipulation. In one embodiment, the first electrode 210 is a woven conductive material that has a circular cross-section that defines a central cavity. In one other embodiment, the first electrode 210 is constructed of a woven conductive material and is substantially spherical in shape, and defines a substantially spherical cavity within the electrode. In yet another embodiment, the first electrode 210 comprises a conductive material in the shape of a helix that defines an opening within the helix. The first electrode 210 may have a lattice configuration, and may be an active electrode.

As discussed above, proximate (meaning near) to the first electrode 210 is the second electrode 220 located on the distal end 212 of the first electrode 210. The second electrode 220 may be constructed of any electrically conductive material, typically a metal. Proximate to the first electrode 210 is the second electrode 220 disposed on the distal end 212 of the first electrode 210, and partially contained within the first electrode 210. A first insulator 240 separates the first electrode 210 from the second electrode 220. A manipulation means 270 is anchored to the second electrode 220. The first electrode 210 is typically an active electrode and the second electrode 220 may be a return electrode.

Also proximate to the first electrode 210 is a third electrode 230. As shown in FIG. 2A, the second electrode 220 and the third electrode 230 are typically positioned on opposite ends of the first electrode 210. The third electrode 230 may be constructed of any electrically conductive material and, like the second electrode 220, can function as an active or return electrode, but is typically used as a return electrode. The third electrode 230 and the first electrode 210 are separated by the second insulator 250. The second insulator 250 may be constructed of a high-temperature, electrically insulating material such as ceramic or silicone.

Typically, in use the second electrode 220 functions as a return electrode, although in certain embodiments the second electrode 220 functions as either a return electrode or an active electrode by switching the polarity of the electrodes. For example, it is possible to switch between having the first electrode 210 and second electrode 220 be the active electrode. In such embodiments the third electrode 230 is typically kept as a return electrode, so as to maintain a ratio where the surface area of return electrodes is significantly greater than the surface area of the active electrodes. The second electrode 220 and the first electrode 210 are separated by the first insulator 240. The first insulator 240 may be constructed of any high-temperature, electrically insulating material such as ceramic or silicone. However, it may be desirable to temporarily remove tissue at the tip of the apparatus 200, in which case switching functionality to allow the second electrode 220 to be the active electrode is desirable, since tissue will be removed most at the tip of the assembly 200.

Figure 2B:
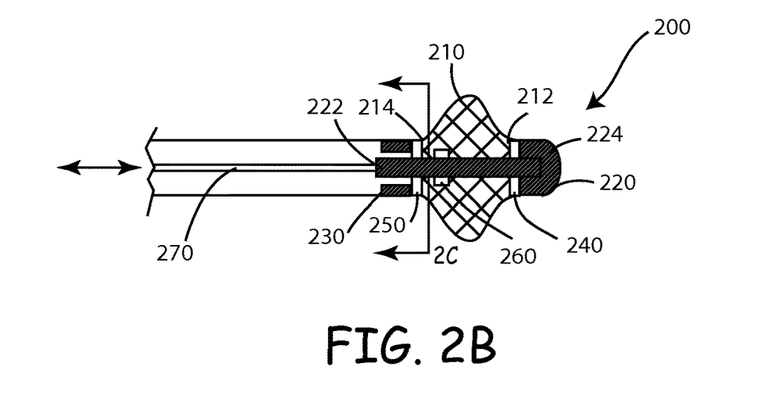
FIG. 2B is a side sectional view of the electrode assembly of FIG. 2A in an alternative position.

FIG. 2B is a side sectional view of the apparatus of FIG. 2A in an alternative position. This view reveals that the second electrode 220, which is partially disposed on the distal end of the first electrode 210, is partially contained within the first electrode 210. In this depicted embodiment, second electrode 220 includes a central shaft 222 that runs down the interior of the first electrode 210 and connects to a wider head 224. This central shaft 222 can be integrally formed with the head 224 of the second electrode 220, such that the second electrode 220 is a single piece. However, in other embodiments this central shaft 222 can be an independent piece, although typically in electrical communication with the head 224.

In the depicted embodiment, a third insulator 260 surrounds the partially contained portion of the second electrode 220 to prevent contact between the first electrode 210 and the second electrode 220. The third insulator 260 may be constructed of a high-temperature, electrically insulating material such as ceramic or silicone, and may be disposed on the second electrode 220. It will be appreciated that third insulator 260 can cover more or less of the second electrode than is shown in FIG. 2B. Also revealed through this side sectional view of the apparatus of FIG. 2A, is that the first insulator 240, the second insulator 250, and the third electrode 230 define respective openings through which the second electrode 220 may pass.

It will be appreciated that the configuration of electrodes shown in FIGS. 2A and 2B is only representative, and that alterations in the configuration of the electrodes can be made without deviating from the spirit and scope of the design. For example, specifically in reference to FIG. 2B, it will be appreciated that the portion of the central shaft 222 of the second electrode 220 surrounded by the first electrode 210 can be shortened significantly, or even eliminated so that none of the second electrode 220 is surrounded by the first electrode 210. Similarly, it is possible to increase the size and/or surface area of any of the electrodes shown in FIGS. 2A and 2B.

Referring again to FIG. 2B, attached to the second electrode 220 is a manipulation means 270. The manipulation means is, in this example, a rod 270 that is in mechanical communication with the first electrode 210 and is anchored to the second electrode 220. Thus, although the rod 270 does not actually touch the first electrode 210, it is in mechanical communication with the first electrode 210 because movement of the rod mechanically changes the shape of the first electrode 210.

In the alternative, the manipulation means 270 may be a rod, screw, solenoid, or similar device that, when engaged, changes the shape, diameter, or surface area of the first electrode 210 by applying a force either directly or indirectly to the first electrode 210. The manipulation means may be engaged through a foot pedal, button, lever, valve, dial, nut, or any other applicable user-apparatus interface. The manipulation means may be a means of changing the diameter of the first electrode 210. The manipulation means also may be a means of changing the shape of the first electrode 210. For example, the manipulation means may be used to create a protrusion in the first electrode along just one side of the electrosurgical apparatus, such as that shown and described later in FIG. 6.

Figure 2C:
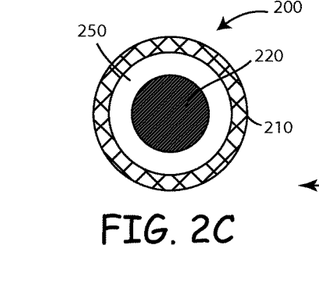
FIG. 2C is a cross sectional view of the electrode assembly of FIG. 2A.

FIG. 2C is a cross sectional view of the electrode assembly 200 of FIG. 2A in the alternative position demonstrated in FIG. 2B. The first electrode 210, being expanded, has a larger diameter than the outside diameter of the second insulator 250. The second electrode 220, a portion of which is partially contained within the first electrode 210, has a smaller diameter than the first electrode, and a smaller diameter than the second insulator 250. The cavity defined by the first electrode 210 is not limited to a circular cross section, and also may have a cross section of virtually any shape. Likewise, the cavity defined by the second insulator 250 need not be circular.

Figure 3A:
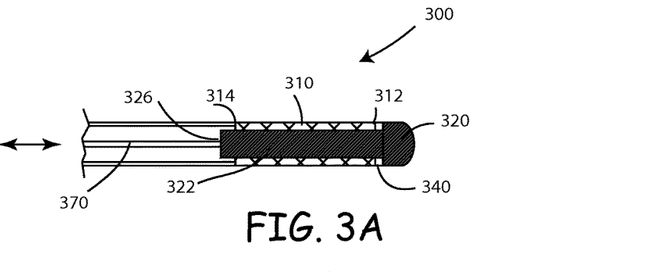
FIG. 3A is a side sectional view of an alternative electrode assembly embodiment consistent with the technology claimed herein.

FIG. 3A is a side sectional view of an alternative embodiment of an electrode assembly 300 made in accordance with an implementation of the invention. This implementation shows the electrode assembly 300 having just first and second electrodes, in which a first electrode 310 partially surrounds a second electrode 320. Proximate to a first electrode 310 is a second electrode 320 disposed on the distal end 312 of the first electrode 310, and partially contained within the first electrode 310. A first insulator 340 separates the first electrode 310 from the second electrode 320. A manipulation means 370 is anchored to the second electrode 320. The first electrode 310 is typically an active electrode and the second electrode 320 may be a return electrode.

While the various apparatuses of the invention will frequently be used to remove tissue, it should be appreciated that the active electrodes can also be readily used to deliver energy at coagulation frequency. The large surface area of the first electrodes 210, 310, etc. allow a broad delivery of coagulation energy, thereby allowing aggressive efforts to stop even relatively large areas of bleeding resulting from tissue removal. Thus, the present invention offers the opportunity to provide quick, wide-area coagulation energy by using the large surface area of the first electrodes 210, 310, etc.

In further review of FIG. 3, a manipulation means 370 is in mechanical communication with the first electrode 310, and is anchored to the second electrode 320 at the end 326 of central shaft 322. The first electrode 310, first insulator 340, second electrode 320, manipulation means 370, and leads or wires 380 are of a similar nature, construct, and materials to those discussed in FIG. 2A, FIG. 2B, and FIG. 2C, above.

Figure 3B:
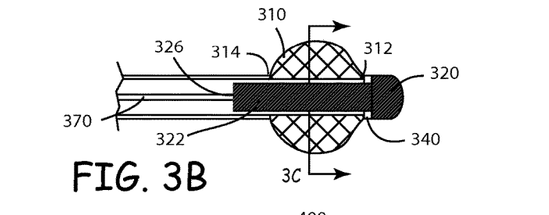
FIG. 3B is a side sectional view of the electrode assembly of FIG. 3A in an alternative position.

FIG. 3B is a side sectional view of the apparatus of FIG. 3A in an alternative position. In FIG. 3B the distal end 312 and proximal end 314 of the first electrode 310 are drawn closer together, thus changing the diameter and shape of the first electrode 310. The manipulation means 370 may be engaged so as to pull the second electrode 320 toward the proximal end 314 of the first electrode 310, thereby compressing the first electrode 310 and causing the change in shape and/or diameter.

Figure 3C:
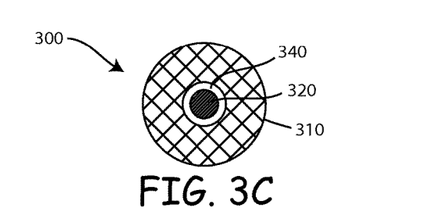
FIG. 3C is a cross sectional view of the electrode assembly of FIG. 3A.

FIG. 3C is a cross sectional view of the apparatus of FIG. 3A in the alternative position demonstrated in FIG. 3B. The first electrode 310 is in a shortened state whereby it becomes wider, and defines a cavity that at least partially contains the second electrode 320.

Figures 4A, 4B, 4C:
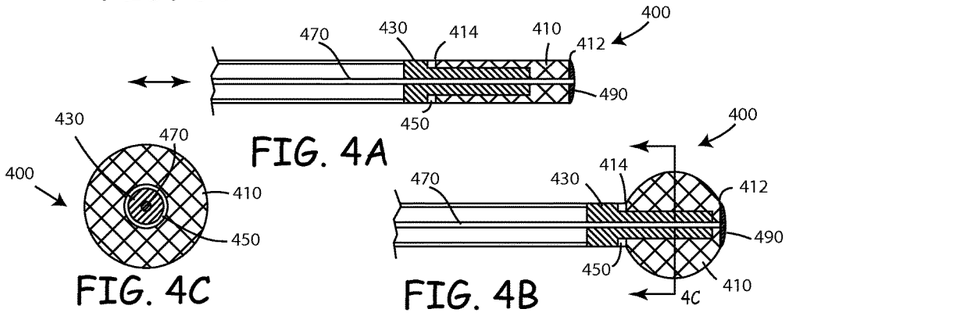
FIG. 4A is a side sectional view of an alternative embodiment electrode assembly consistent with the technology claimed herein.
FIG. 4B is a side sectional view of the apparatus of FIG. 4A in an alternative position.
FIG. 4C is a cross sectional view of the apparatus of FIG. 4A.

FIG. 4A is a side sectional view of an alternative embodiment consistent with the technology of the present invention. Proximate to a first electrode 410 is a second electrode 430 disposed near (or proximate to) the proximal end of the first electrode 410. Separating the first electrode 410 from the second electrode 430 is a first insulator 450. In mechanical communication with the first electrode 410 is a manipulation means 470, which extends from a lead or wire to the distal end of the first electrode 410. The manipulation means 470 may be slidably disposed within the first electrode 410 and anchored to the tip 490 on the distal end of the first electrode 410. The first electrode 410, first insulator 450, second electrode 430, manipulation means 470, and leads or wires are of a similar nature, construction, and materials to those discussed in FIG. 2A, FIG. 2B, and FIG. 2C, above.

The tip 490 may be an extension of the manipulation means 470, or may be a separate entity constructed out of any material that allows the manipulation means 470 to be anchored to the distal end of the first electrode 410. The tip 490 may also be a portion of the first electrode 410, and be constructed out of substantially similar material, or the tip 490 can be an extension of either the first electrode 410 or the manipulation means 470. Thus, electrode assembly 400 contains two electrodes: An outer electrode (the first electrode 410) plus a substantially surrounded inner electrode (the second electrode 430).

FIG. 4B is a side sectional view of the apparatus of FIG. 4A in an alternative position. In FIG. 4B the distal end 412 of the first electrode has been drawn closer to the proximal end 414 than in FIG. 4A, thus changing the diameter and shape of the first electrode 410. The manipulation means 470 may be engaged so as to pull the tip 490 closer to the proximal end of the first electrode 410, thereby compressing the first electrode 410 and causing a change in diameter.

FIG. 4C is a cross sectional view of the apparatus of FIG. 4A in the alternative position demonstrated in FIG. 4B. The first electrode 410 is in an expanded state and defines a cavity that at least partially contains the second electrode 430. The first insulator 450 separates the first electrode from the second electrode 430. Thus, the second electrode 430 may define a passage through which the manipulation means 470 is disposed. The passage need not have a circular cross section as shown in FIGS. 4B and 4C, but could be a variety of shapes that allow sliding or shifting in position of the manipulation means 470. The passage also need not be in the center of the second electrode 430, but could be positioned anywhere through the second electrode 430 so long as the passage allows sliding or shifting of the manipulation means 470.

Figures 5A, 5B, 5C:
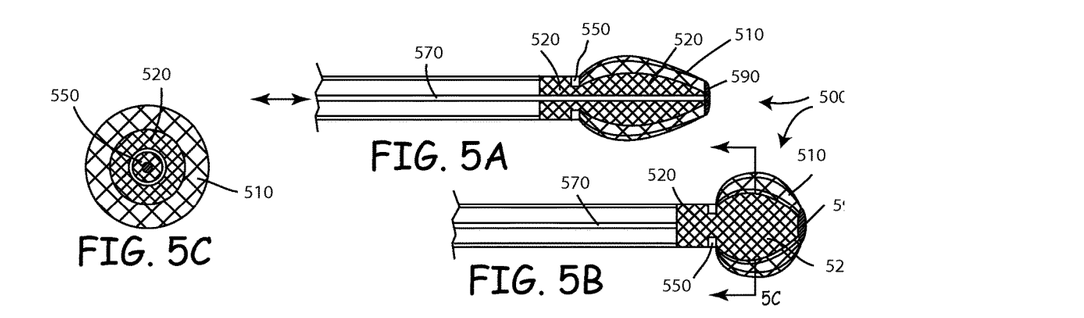
FIG. 5A is a side sectional view of an alternative embodiment consistent with the technology claimed herein.
FIG. 5B is a side sectional view of the apparatus of FIG. 5A in an alternative position.
FIG. 5C is a cross sectional view of the apparatus of FIG. 5A.

FIG. 5A is a side sectional view of an alternative embodiment consistent with the technology claimed herein. Separating a first electrode 510 and a second electrode 520 is a first insulator 550. A manipulation means 570 extends through a passage within the first electrode 510 and the second electrode 520. Proximate to the first electrode 510 is the second electrode 520 disposed proximate to the proximal end of the first electrode 510. The second electrode 520 is also at least partially contained by the first electrode 510. In this embodiment, the second electrode 520 is, like the first electrode 510, constructed so as to be flexible, to define at least a partial cavity within the electrode, and has a proximal end and a distal end. The second electrode 520 is not limited to a circular cross section, and may have a cross section of virtually any shape. The second electrode 520 may be at least partially constructed of coiled wire, braided electrically conductive material, woven electrically conductive material, or any combination thereof. The second electrode 520 can also be at least partially constructed of any other conductive material where structural flexibility is allowed for shape manipulation. The second electrode 520 may have a lattice configuration, and may be return electrode.

As shown, the second electrode 520 may have a distal end that shares a tip 590 with the distal end of the first electrode 510. If so, then a second insulator would be used to prevent contact between the distal end of the first electrode 510 and the distal end of the second electrode 520. The manipulation means 570 then extends through the passage of the first electrode 510 and the second electrode 520 to the tip of the apparatus. In an alternative embodiment, the second electrode does not share a tip 590 with the first electrode, and has a distal end that is separate from the distal end of the first electrode 510. In such a situation the manipulation means 570 may extend into the passage though the first electrode 510 and the second electrode 520, and then extend through the distal end of the second electrode 520 to the tip 590 of the first electrode 510.

The first electrode 510, first insulator 550, manipulation means 570, and leads or wires are of a similar nature, construct, and materials to those discussed in FIG. 2A, FIG. 2B, and FIG. 2C, above.

FIG. 5B is a side sectional view of the electrode assembly 500 of FIG. 5A in an alternative position. In FIG. 5B the distal end is positioned closer to the proximal end of the first electrode 510 and the second electrode 520 than in FIG. 5A, thus changing the diameter and shape of the first electrode 510. The manipulation means 570 may be engaged so as to pull the tip 590 closer to the proximal end of the first electrode 510, thereby compressing the first electrode 510 and the second electrode 520, causing a change in shape or diameter. In this embodiment of an electrode assembly 500, the diameter of the second electrode 520 changes in substantially the same proportion to the first electrode 510.

FIG. 5C is a cross sectional view of the apparatus of FIG. 5A in the alternative position demonstrated in FIG. 5B. The first electrode 510 is in an expanded state and defines a passage that at least partially contains the second electrode 520. The second electrode 520 is also in an expanded state and defines a cavity that at least partially contains the manipulation means 570. The first insulator 550 separates the first electrode 510 from the second electrode 520, and defines a passage that at least partially contains the manipulation means 570.

Figure 6A:
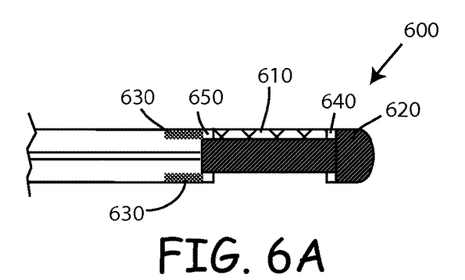
FIG. 6A is a side sectional view of an alternative embodiment consistent with the technology claimed herein.

FIG. 6A is a side sectional view of an alternative embodiment for an electrode assembly 600, the assembly constructed consistent with the technology claimed herein. Also proximate to the first electrode 610 is a second electrode 620 partially disposed on the distal end of the first electrode 610, and also partially contained within the first electrode 610. The first electrode 610 may be an active electrode and the second electrode 620 may be a return electrode. The second electrode 620 and the first electrode 610 are separated by a first insulator 640.

The manipulation means 670 is in mechanical communication with the first electrode 610, and is anchored to the second electrode 620. The manipulation means 670 may be at least partially disposed in leads or wires 680 connected to the apparatus 600. The first electrode 610, first insulator 640, second electrode 620, manipulation means 670, and leads or wires 680 are of a similar nature, construct, and materials to those discussed in FIG. 2A, FIG. 2B, and FIG. 2C, above.

Figure 6B:
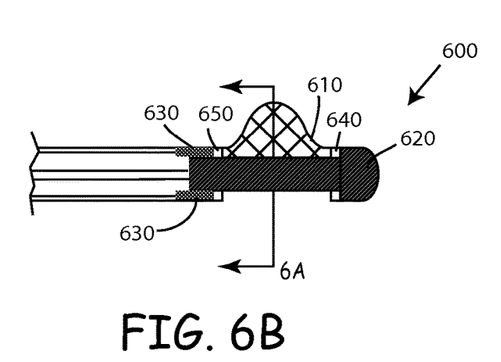
FIG. 6B is a side sectional view of the apparatus of FIG. 6A in an alternative position.

FIG. 6B is a side sectional view of the apparatus of FIG. 6A in an alternative position. In FIG. 6B the distal end is positioned closer to the proximal end of the first electrode 610 than in FIG. 6A, thus changing the diameter and shape of the first electrode 610. The manipulation means 670 may be engaged so as to pull the second electrode 620 closer to the proximal end of the first electrode 610, thereby compressing the first electrode 610 and causing a change in shape. In this embodiment the apparatus 600 is asymmetrical and may be relevant for asymmetrical tissue requiring electrosurgery.

Figure 6C:
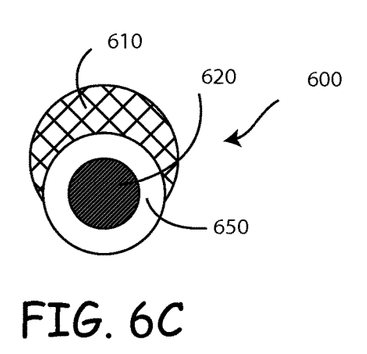
FIG. 6C is a cross sectional view of the apparatus of FIG. 6A.

FIG. 6C is a cross sectional view of the apparatus of FIG. 6A in the alternative position demonstrated in FIG. 6B. The first electrode 610 is in an expanded state and defines an opening that at least partially contains the second electrode 620.

Figure 7A:
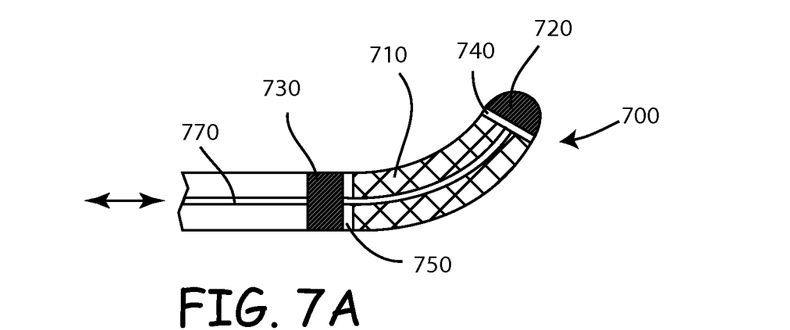
FIG. 7A is a side view of an alternative embodiment consistent with the technology claimed herein.

FIG. 7A is a side view of an alternative embodiment consistent with the technology claimed herein. Proximate to a first electrode 710 is a second electrode 720 at least partially disposed on the distal end of the first electrode 710. The second electrode 720 and the first electrode 710 are separated by a first insulator 740. Also proximate to the first electrode 710 is a third electrode 730. The third electrode 730 and the first electrode 710 are separated by a second insulator 750. A manipulation means 770 is in mechanical communication with the first electrode 710, and is anchored to the second electrode 720. The manipulation means 770 may be at least partially disposed in leads or wires connected to the apparatus 700. In this illustrative embodiment, the first electrode 710, and the manipulation means 770 are curved so as to form an asymmetrical electrode assembly 700.

It will be appreciated that the first electrode 710 may be flexible, but formed such that the electrode is curved in its natural or at rest state, or that the electrode is configured to be moved between curved and straight positions. Thus, the electrode can be deflectable, such as to be steerable, or the electrode can be permanently made to encompass a curve. One advantage of such deflected and deflectable electrode assemblies is that they can be used to aid navigation of partially obstructed passageways and non-linear passageways more easily than a straight assembly. In addition, the deflected shapes (i.e, the non-linear shapes), can be used advantageously for some tissue removal and coagulation processes, improving precision and effectiveness by allowing access to areas that might be off-axis form the apparatus, and would thus be more difficult to reach with a straight electrode assembly.

Figure 7B:
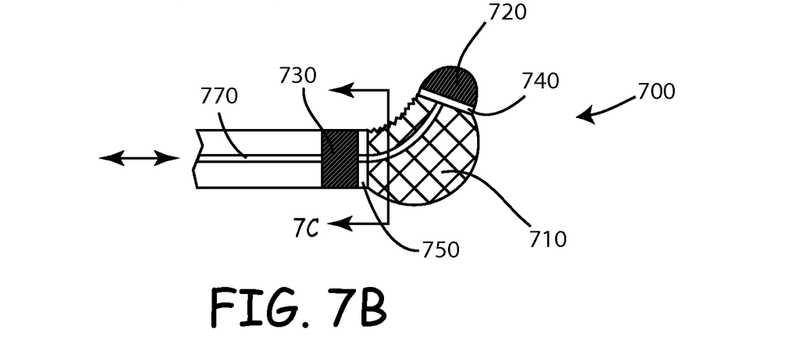
FIG. 7B is a side sectional view of the apparatus of FIG. 7A in an alternative position.

FIG. 7B is a side sectional view of the apparatus of FIG. 7A in an alternative position. In FIG. 7B the distal end is positioned closer to the proximal end of the first electrode 710 than in FIG. 7A, thus changing the diameter and shape of the first electrode 710. The manipulation means 770 may be engaged so as to pull the second electrode 720 closer to the proximal end of the first electrode 710, thereby compressing the first electrode 710 and causing the change in diameter. FIG. 7B illustrates that there may be asymmetrical expansion of the apparatus 700.

Figure 7C:
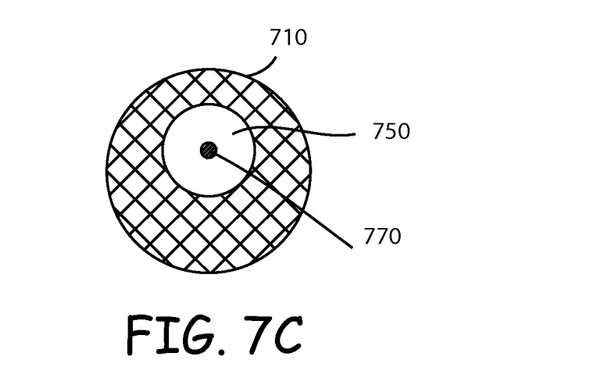
FIG. 7C is a cross sectional view of the apparatus of FIG. 7A.
Figure 8A:
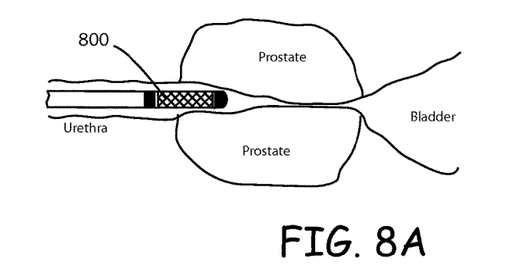
FIG. 8A is a side view of use of an example implementation of the apparatus of the invention, showing the apparatus inserted into a representation of an expanded prostate, prior to removal of any prostate tissue.
Figure 8B:
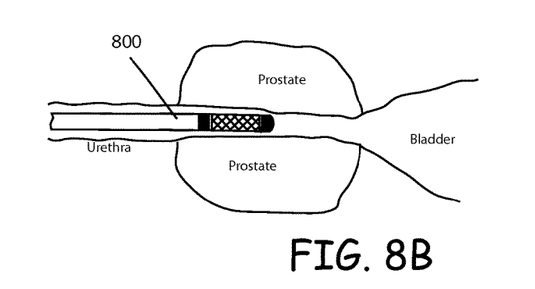
FIG. 8B is a side view of use of an example implementation of the apparatus of the invention, showing the apparatus inserted into a representation of an expanded prostate after removal of some prostate tissue.
Figure 8C:
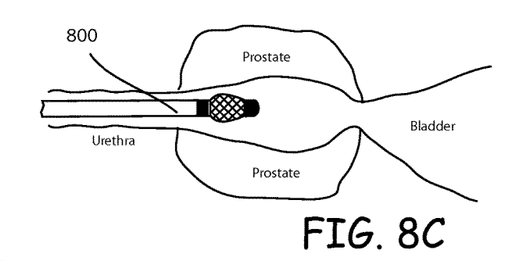
FIG. 8C is a side view of use of an example implementation of the apparatus of the invention, showing the apparatus inserted into a representation of an expanded prostate and showing the apparatus with an expanded active electrode to further remove prostate tissue.
Figure 8D:
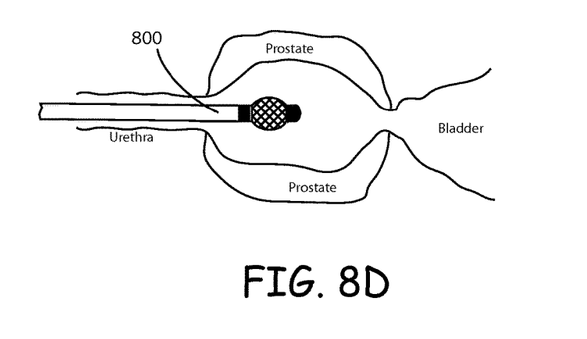
FIG. 8D is a side view of use of an example implementation of the apparatus of the invention, showing the apparatus inserted into a representation of an expanded prostate and showing the apparatus with an expanded active electrode to further remove prostate tissue.

FIG. 7C is a cross sectional view of the apparatus of FIG. 7A in the alternative position demonstrated in FIG. 7B. The first electrode 710 is in an expanded state and defines a passage that at least partially contains the manipulation means 770. The second insulator 750 that separates the first electrode 710 from the third electrode 730 defines a cavity that at least partially contains the manipulation means 770.

FIG. 8 is a diagram of an example implementation consistent with the technology claimed herein and according to various embodiments. The example implementation demonstrates use of various embodiments of the technology disclosed herein to remove prostatic tissue associated with benign prostatic hyperplasia (BPH), for example. The example implementation discussed is merely for explicative purposes rather than limiting purposes.

The apparatus may be inserted into a urethra in a relatively unexpanded state so as to extend into the urethra to the site where electrosurgery will take place. The illustrated urethra includes a narrowing or occlusion, which is desirably widened or removed. Insertion may be similar to urinary catheterization.

When apparatus is extended to the site of the electrosurgery, the apparatus may be engaged for tissue removal. The apparatus may be engaged through a user-apparatus interface such as a foot pedal, button, valve, dial, nut, or any other applicable user-apparatus interface that is in communication with the electrosurgical generator. The frequency of the electricity may be selected for ablation or coagulation, or both.

As the tissue is removed, the apparatus may be expanded to increase the working diameter of the apparatus. Expansion may occur through a user-apparatus interface such as a foot pedal, button, valve, dial, nut, or any other applicable user-apparatus interface that is in communication with the manipulation means, discussed through FIGS. 2-7, above. A greater working diameter of the apparatus improves tissue removal, including precision of removal, so as to create a greater internal passageway through the prostate. When the surgery session is ended, the apparatus may be contracted again to provide relative ease in the removal of the device.

The method demonstrated in FIG. 8 is merely one example implementation of the technology disclosed herein. The technology could also be used for other open, laproscopic, or endoluminal surgical procedures. Thus, FIG. 8A is a side view of use of an example implementation of the apparatus of the invention, showing the apparatus inserted into a urethra, prior to removal of any tissue at the narrowing caused by prostate tissue. FIG. 8B is a side view of use of an example implementation of the apparatus of the invention, showing the apparatus inserted into a urethra, after removal of any tissue at the narrowing has started. FIG. 8C is a side view of use of an example implementation of the apparatus of the invention, showing after removal of any tissue at the narrowing has started, with an expanded active electrode to further remove prostate tissue. FIG. 8D is a side view of use of an example implementation of the apparatus of the invention, showing the apparatus showing the apparatus with an expanded active electrode to further remove tissue (or to apply coagulation energy.

Figure 9:
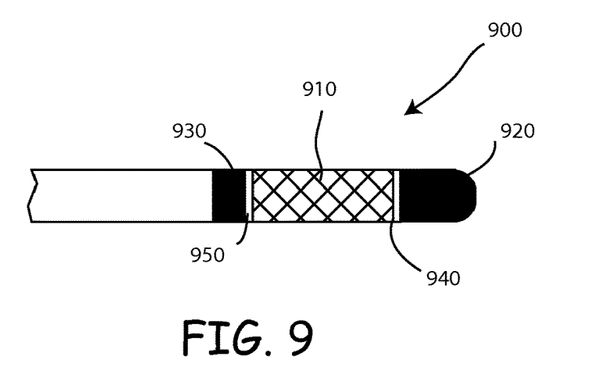
FIG. 9 is a side sectional view of an alternative embodiment consistent with the technology claimed herein.

FIG. 9 is a side sectional view of an alternative embodiment assembly 900 consistent with the technology claimed herein, wherein first electrode 910 has second electrode 920 and third electrode 930 positioned on alternative ends. In this embodiment, second electrode 920 has significantly more surface area than third electrode 930. It will be appreciated, however, as discussed earlier in this application, that the size difference may be reversed, so that the second electrode has significantly less surface area than the third electrode. Also shown are first and second insulators, 940 and 950. In the embodiment shown in FIG. 9, the energy delivered to each electrode can be adjusted to control the location and nature of delivered energy. In most embodiments the first electrode 910 is active, while the second electrode 920 and third electrode 930 are returns. However, the function of the first and second electrodes can be reversed, so that the second electrode 920 is active and the first electrode 910 is a return (along with the third electrode 920, which would typically remain as a return electrode so as to maintain significantly greater surface area for the return electrodes). The alternation of function between the first and second electrodes can be automatic or manual. Also, it can be cycled rapidly to create a boring electrode that both cuts at the tip (second electrode 920) and at the sides (first electrode 910). Notably, it is also possible to switch the third electrode into this rotation, such that the third electrode 930 becomes active while the first and second electrodes 910, 920 are returns. Also, it will be appreciated that any and all of these electrodes can be used to deliver coagulation energy, not just ablation energy. In one desirable mode, coagulation energy is delivered between the second and third electrodes 920, 930.

Figure 10A:
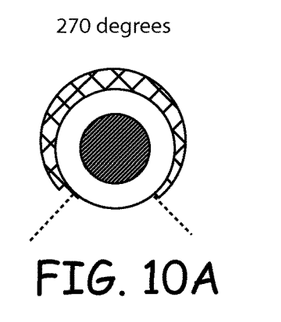
FIG. 10A is a cross sectional view of an example implementation of the apparatus of the invention.
Figure 10B:
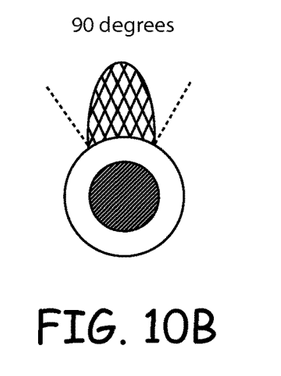
FIG. 10B is a cross sectional view of an example implementation of the apparatus of the invention.
Figure 10C:
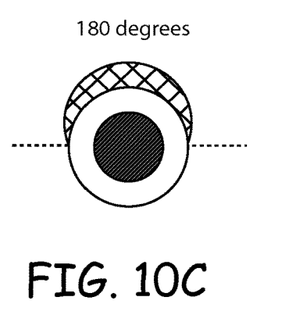
FIG. 10C is a cross sectional view of an example implementation of the apparatus of the invention.

FIGS. 10A to 10C are cross sectional views of example implementations of the invention, showing different configurations for first electrodes. In FIG. 10A, the first electrode extends about 270 degrees around the outside of the assembly; the first electrode extends about 90 degrees around the assembly of FIG. 10B; and the first electrode extends about 180 degrees around the outside of the assembly of FIG. 10C. The approximate extent of the electrodes is shown by dashed lines. It will be appreciated, as shown in these examples, that various shapes of first electrodes can be used, and the first electrodes can be configured to cover relatively large or small parts of the circumference of the electrode assembly.

What is claimed is:

1. An electrosurgical apparatus for removal of tissue from a patient, the electrosurgical apparatus comprising: an electrosurgical generator; an electrode assembly; a cable having a proximal end connected to the electrosurgical generator and a distal end connected to the electrode assembly; a user-apparatus interface in communication with the electrosurgical generator and the electrode assembly; the electrode assembly including: a first electrode having a proximal end and a distal end; a second electrode at least partially disposed proximate to the distal end of the first electrode; and a third electrode at least partially disposed proximate to the proximal end of the first electrode; the first electrode having a smaller surface area than the combined surface areas of the second electrode and third electrode; wherein the electrosurgical apparatus comprises a means configured such that the user-apparatus interface provides for operation of the electrode assembly in a first mode wherein the first electrode is configured as an active electrode for the removal of tissue and the second and third electrodes comprise a combined passive electrode, such that the tissue removal occurs primarily in proximity to the first electrode and the tissue removal occurs through vaporization by formation of a plasma.

2. The electrosurgical apparatus of claim 1, wherein the first electrode is positioned substantially intermediate the second and third electrodes.

3. The electrosurgical apparatus of claim 1, wherein the first electrode is separated from the second and third electrodes by at least one insulator.

4. The electrosurgical apparatus of claim 1, wherein the first electrode is generally axially symmetric in shape.

5. The electrosurgical apparatus of claim 1 wherein the first electrode comprises a conductive lattice.

6. The electrosurgical apparatus of claim 1, further comprising a manipulation means in mechanical communication with the first electrode assembly, the manipulation means configured to apply a mechanical force to change the shape of the first electrode.

7. The electrical apparatus of claim 6 wherein the first electrode shape change results in an increase of its effective vaporization zone without any substantial change in the active electrode surface area.

8. The electrical apparatus of claim 6 wherein the first electrode shape change is in the form of a bulge that is one-sided, axially non-uniform in nature.

9. The electrosurgical apparatus of claim 1, wherein at least a portion of the second electrode is surrounded by the first electrode.

10. The electrosurgical apparatus of claim 1, wherein at least a portion of the third electrode is surrounded by the first electrode.

11. The electrosurgical apparatus of claim 1, wherein the first electrode has a surface area and the second and third electrodes have the combined surface area, and the ratio of the first electrode surface area to the combined second and third electrode surface area is less than 1:2.

12. The electrosurgical apparatus of claim 1, wherein the second and third electrodes are of unequal surface area.

13. The electrosurgical apparatus of claim 1, wherein the first electrode has an active surface extending less than 270 degrees axially around the electrode.

14. The electrosurgical apparatus of claim 1, wherein the first electrode has a first mode of use wherein the electrode is generally axially symmetric in shape, and a second mode of use wherein the first electrode shape has been changed such that the first electrode has a generally axially asymmetric shape.

15. The electrosurgical apparatus of claim 14, wherein active surface area of the first electrode in the first and second modes of use is substantially constant.

16. The electrosurgical apparatus of claim 15, wherein a vaporization zone around the first electrode increases in size from the first mode to the second mode.

17. A method for removal of tissue from a patient using a plasma, the method comprising:
   providing an electrosurgical device comprising:
      a) an electrosurgical generator;
      b) an electrode assembly, the electrode assembly comprising:
         a first electrode having a proximal end and a distal end,
         a second electrode at least partially disposed proximate to the distal end of the first electrode, and
         a third electrode at least partially disposed proximate to the proximal end of the first electrode; and
      c) a user-apparatus interface in communication with the electrosurgical generator and the electrode assembly:
   inserting the electrosurgical device into a site where electrosurgery will take place;
   engaging the user-apparatus interface to deliver electrical energy from the electrosurgical generator to form a plasma at the first electrode such that the electrosurgical device is in a first mode such that the first electrode is active, the second electrode and the third electrode form a combined return electrode, such that the tissue removal occurs in proximity to the first electrode;
   engaging the user-apparatus interface to deliver electrical energy from the electrosurgical generator to form a plasma at the second electrode such that the electrosurgical device in a second mode such that the second electrode is active, and the first electrode and the third electrode comprise a combined return electrode such that the tissue removal occurs in proximity to the second electrode; and
   switching between the first mode and second mode; and
   wherein the first electrode has a smaller surface area than the combined surface areas of the second electrode and third electrode; and
   wherein the second electrode has a smaller surface area than the combined surface areas of the first electrode and third electrode.

18. The method of claim 17, further comprising:
   engaging the electrosurgical device in a third mode such that the first electrode is return, the second electrode is return, and the third electrode is active; and
   switching between the first mode, second mode, and third mode.

19. The method of claim 17, wherein at least one of the first, second, or third electrodes is deformable.

20. A method for removal of tissue from a patient, the method comprising:
   providing an electrosurgical device comprising:
      an electrosurgical generator;
      an electrode assembly, the electrode assembly comprising:
         a first electrode having a proximal end and a distal end,
         a second electrode at least partially disposed proximate to the distal end of the first electrode, and
         a third electrode at least partially disposed proximate to the proximal end of the first electrode;
      a user-apparatus interface in communication with the electrosurgical generator and the electrode assembly;
   inserting the electrosurgical device into a site where electrosurgery will take place; and
   engaging the user-apparatus interface to deliver electrical energy from the electrosurgical generator to form a plasma at the first electrode such that the electrosurgical device in a first mode such that the first electrode is active and the second electrode and the third electrode form a combined return electrode, such that the plasma is formed and the tissue removal occurs primarily in proximity to the first electrode;
   wherein the first electrode has a smaller surface area than the combined surface areas of the second electrode and third electrode.

21. The method for removal of tissue of claim 20, wherein the first electrode has an active surface extending less than 270 degrees axially around the electrode.

22. The electrosurgical apparatus of claim 20, wherein at least a portion of the exposed surface of the return electrode is not capable of direct tissue contact.

23. The electrosurgical apparatus of claim 20, wherein the first electrode is configured to change shape resulting in an increase of its effective vaporization zone without any substantial change in the active electrode to return electrode surface area ratio.

* * * * *